US009023045B2

(12) United States Patent
Lehmann et al.

(10) Patent No.: US 9,023,045 B2
(45) Date of Patent: May 5, 2015

(54) BOLT AND TOOL WITH ANTI-TORQUE FEATURES

(71) Applicant: Stryker Trauma SA, Selzach (CH)

(72) Inventors: Philippe Lehmann, Lamboing (CH); Joël Bouquet, Solothurn (CH); Esther Wobmann, Solothurn (CH); Markus Behrens, Monnaz (CH)

(73) Assignee: Stryker Trauma SA (CH)

( * ) Notice: Subject to any disclaimer, the term of this patent is extended or adjusted under 35 U.S.C. 154(b) by 158 days.

(21) Appl. No.: 13/770,042

(22) Filed: Feb. 19, 2013

(65) Prior Publication Data

US 2013/0165930 A1     Jun. 27, 2013

Related U.S. Application Data

(63) Continuation-in-part of application No. 13/275,714, filed on Oct. 18, 2011, now Pat. No. 8,679,117.

(30) Foreign Application Priority Data

Oct. 28, 2010   (EP) .................................... 10189212

(51) Int. Cl.
*A61B 17/00* (2006.01)
*A61F 4/00* (2006.01)
(Continued)

(52) U.S. Cl.
CPC ................ *A61B 17/60* (2013.01); *A61B 17/62* (2013.01); *A61B 17/6441* (2013.01); *A61B 17/8861* (2013.01); *A61B 17/8869* (2013.01); *A61B 17/8875* (2013.01)

(58) Field of Classification Search
CPC . A61B 17/62; A61B 17/6458; A61B 17/6466

USPC ........... 606/56, 59, 300–321, 54; 411/1, 3, 4, 411/106, 107, 338, 355, 366.1, 378–426

See application file for complete search history.

(56) References Cited

U.S. PATENT DOCUMENTS 2,333,033 A    10/1943  Mraz
2,854,981 A    10/1958  Morrison
(Continued)

FOREIGN PATENT DOCUMENTS

CN    2607109 Y    3/2004
WO    9106253 A1   5/1991
(Continued)

OTHER PUBLICATIONS

TrueLok Ring Fixation System, General Principles, May 2010.
(Continued)

*Primary Examiner* — Ellen C Hammond
*Assistant Examiner* — Christina Negrellirodrigue
(74) *Attorney, Agent, or Firm* — Lerner, David, Littenberg, Krumholz & Mentlik, LLP

(57) ABSTRACT

A system for fixing a wire to a surface of an external fixator having a wire adapted to extend through bony structure fastened with respect to the surface. A bolt having a shaft which comprises a threaded section, a head section and at least one clamping element is provided wherein the bolt is adapted to extend through an opening in the external fixation element with a nut, and clamps the wire to the surface. A counter torque tool is used to provide a counter torque while fastening the wire with the bolt and the nut. The bolt comprises a counter torque opening and wherein the counter torque tool comprises a section which is adapted to engage into the counter torque opening of the bolt to apply the counter torque.

15 Claims, 8 Drawing Sheets

(51) Int. Cl.
*A61F 5/04* (2006.01)
*A61B 17/60* (2006.01)
*A61B 17/62* (2006.01)
*A61B 17/64* (2006.01)
*A61B 17/88* (2006.01)

(56) References Cited

U.S. PATENT DOCUMENTS

| | | | |
|---|---|---|---|
| 4,624,249 | A | 11/1986 | Alvarez Cambras |
| 4,768,524 | A | 9/1988 | Hardy |
| 4,784,125 | A | 11/1988 | Monticelli et al. |
| 5,431,659 | A | 7/1995 | Ross, Jr. et al. |
| 5,540,686 | A | 7/1996 | Zippel et al. |
| 5,624,440 | A | 4/1997 | Huebner |
| 5,630,814 | A * | 5/1997 | Ross et al. ............ 606/59 |
| 5,702,389 | A | 12/1997 | Taylor et al. |
| 6,689,140 | B2 | 2/2004 | Cohen |
| 7,241,074 | B2 | 7/2007 | Thomke et al. |
| 8,096,998 | B2 | 1/2012 | Cresina |
| 2006/0184169 | A1 | 8/2006 | Stevens |
| 2009/0082776 | A1 | 3/2009 | Cresina |
| 2009/0157125 | A1 | 6/2009 | Hoffman et al. |
| 2011/0082458 | A1 | 4/2011 | Crozet et al. |
| 2011/0196380 | A1 | 8/2011 | Cremer et al. |
| 2012/0184958 | A1 | 7/2012 | Knuchel et al. |

FOREIGN PATENT DOCUMENTS

| | | |
|---|---|---|
| WO | 9505127 A2 | 2/1995 |
| WO | 02053038 A2 | 7/2002 |

OTHER PUBLICATIONS

EP Search report for EP10189212 dated Feb. 18, 2011.
TenXor External Fixation System, Stryker 2009.
Chinese Office Action for Application No. 201110328993.1 dated Sep. 3, 2014.

* cited by examiner

BOLT AND TOOL WITH ANTI-TORQUE FEATURES

CROSS-REFERENCE TO RELATED APPLICATION

The present application is a continuation-in-part of U.S. patent application Ser. No. 13/275,714, filed Oct. 18, 2011, which application claims priority from European Patent Application No. EP 10 189 212.3 filed Oct. 28, 2010, the disclosures of which are hereby incorporated herein by reference.

BACKGROUND OF THE INVENTION

The present invention relates to a bolt for use with an external fixator system which simplifies the fixation of a wire to the frame of the external fixator.

Currently, there are many bone deformities or fractures that external fixators can correct. Such fixators are known, for example, as Ilizarov apparatus.

Usually such an external fixator comprises rings also designated as fixation plates connected by threaded rods or struts to manipulate angulations, translation and length discrepancies of bones. Furthermore the fixation plates are in connection with bony structure by means of wires or pins which usually extend through the rings. The wires or pins are in connection with the plates by means of bolts and nuts. Furthermore the wires have to be tensioned before a fixed connection will be established by means of the bolts and the nuts which leads to a very complicated procedure for the surgeon as several tools have to be used.

First of all the wire has to be fixed by means of a bolt and a nut on one end. Thereby a first wrench has to be used to tighten and a second wrench has to be used to provide a counter torque against the tightening torque.

Afterwards the wire has to be tensioned by means of a wire tensioner and to be secured on the other end. In order to secure the wire two wrenches also have to be used. This means that three tools are used to fix the wire at the second end, namely the wire tensioner and the two wrenches. This is very cumbersome for the surgeon as at least one further person is needed to fix the wire and also the limited space situation leads to difficulties.

Such a prior art system is shown by FIG. 1 from it can be seen that three different tools are used to tighten and to fix the wire to the ring or plate of an external fixator. Thereby a wire tensioner has to be used to tension the wire. The wire tensioner here is designated with reference numeral 5. Furthermore two wrenches have to be used to tighten the bolt and the nut. This means that at least two persons are necessary to tension and to fix the wire. Usually one person manipulates the wire tensioner, whereas the other person handles the wrenches.

A further problem arises when the bolts and nuts have to be re-tightened afterwards it is very likely that there is slight rotation of the opening within the bolt through which the wire extends and therefore the wire looses its alignment.

BRIEF SUMMARY OF THE INVENTION

It is therefore an aspect of the present invention to provide an external fixator system which overcomes the disadvantages of prior art.

Such an aspect is achieved by a system for fixing a wire to an external fixator element wherein the system comprises:

an external fixator element having at least one surface and at least one opening extending from the surface,
a wire adapted to extend through bony structure and to be fastened to the surface,
a bolt having a shaft which comprises a threaded section, a head section and at least one clamping element wherein the bolt is adapted to extend through the opening and the at least one clamping element accommodates and clamps a wire to the surface with a clamping force,
a nut to pull the bolt against the surface the external fixator element with the clamping force, and
a counter torque tool to provide a counter torque while fastening the wire with the bolt and the nut to the surface.

Wherein the bolt comprises a counter torque opening and in that the counter torque tool comprises a bolt section which is adapted to engage into the counter torque opening of the bolt, and wherein the bolt section has preferably a cross-section which is complementary to the counter torque opening.

With such a system it is possible to clamp a wire without using several different tools. Thereby the surgeon can tension the wire without assistance. Preferably the counter torque tool comprises at least one opening through which a part of the wire extends. Thereby the opening serves as protection element for the surgeon since it is preferably provided such that the wire is fully encompassed by the opening. Preferably the counter torque tool comprises a handle which can be held by the surgeon.

Preferably the system further comprises a wire tensioning tool and the counter torque tool comprises a connection section via which the counter torque tool is connectable to the wire tensioning tool, whereby the connection section is preferably a threaded structure. With such an integrated structure the surgeon is able to tension and to fix the wire to the fixation plate without the assistance of a further person.

Preferably the at least one clamping element is arranged closer to the surface than the counter-torque opening. Preferably the counter torque opening extends along a middle axis which extends angular in particular substantially perpendicular to the middle axis of the bolt. Preferably the counter torque opening is provided as a through opening or as a blind opening, whereby the head section encompasses the opening.

Another embodiment of the invention is a system for fixing a position of a wire with respect to a ring member of an external fixation frame, the ring member having top and bottom surfaces. The system comprises at least a bolt and a washer. The washer has a head portion and a shaft portion along a longitudinal axis thereof, the bolt having a recess therein, the recess having a longitudinal axis transverse and offset to the longitudinal axis of the bolt, the shaft portion of the bolt includes a threaded section. The washer has a top surface and a bottom surface and a borehole through the top and bottom surfaces. The shaft portion the bolt is adapted to extend through the borehole of the washer and an opening of the ring member of the external fixation frame when the bottom surface of the washer lies adjacent to the top surface of the ring member. A portion of the wire is at least partially received within the recess of the bolt and is clamped between the head portion of the bolt and the top surface of the washer as a nut is threaded on the threaded section of the shaft portion and a top surface of the nut becomes engaged to the bottom surface of the ring member.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 1:
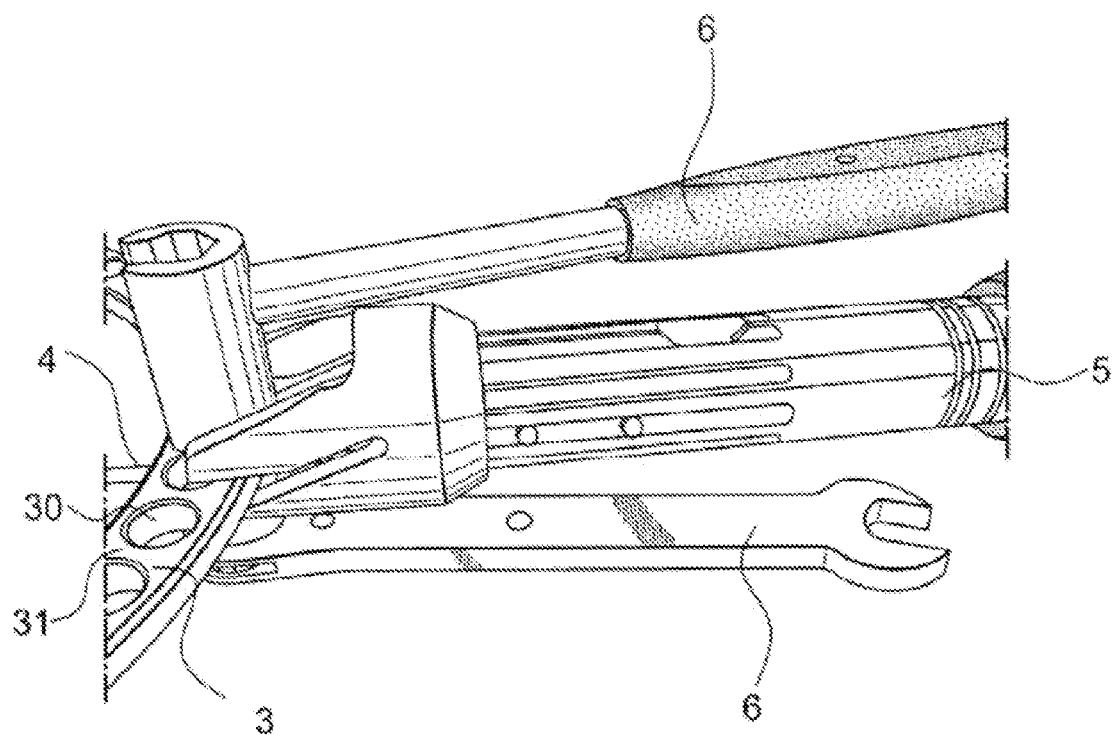
FIG. 1 shows a perspective view of a part of prior art external fixator whereby a wire is to be attached to the external fixator under a tensioning and fixation scheme as known from prior art.

FIG. 1 shows a perspective view of a typical external fixator system. The external fixator system comprises here a plate 3 in the shape of a ring having several openings 30 and a wire 4 which is to be tensioned and to be attached to ring 3. A bolt 1 and a nut may be used with the plate 3. In this prior art scheme the wire is tensioned by a wire tensioner 5 and afterwards the bolt and the nut are tightened by means of two wrenches 6, whereby one of the wrenches is in connection with the bolt and the other one with the nut.

Figure 2:
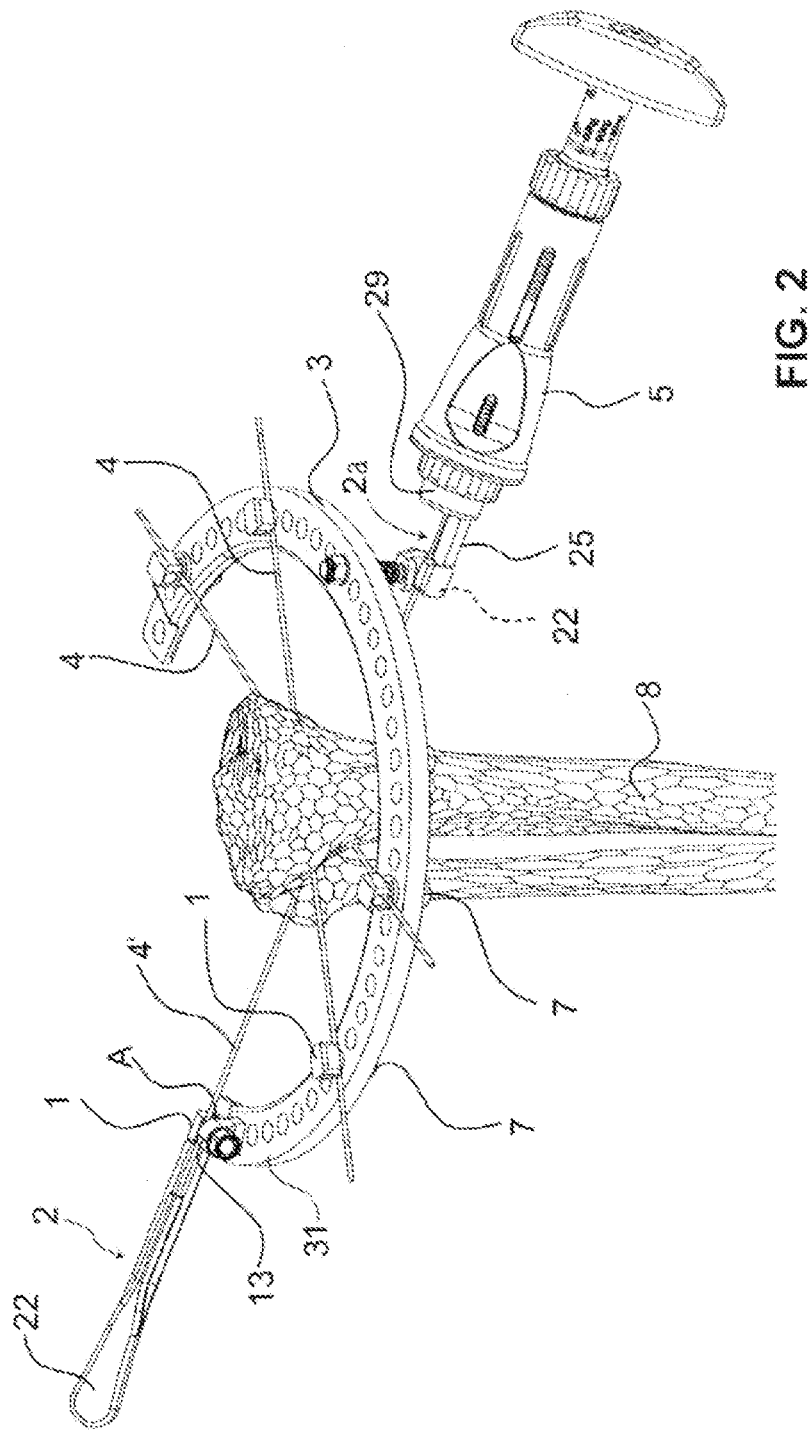
FIG. 2 shows an external fixator system using a tool of the present invention.
Figure 3:
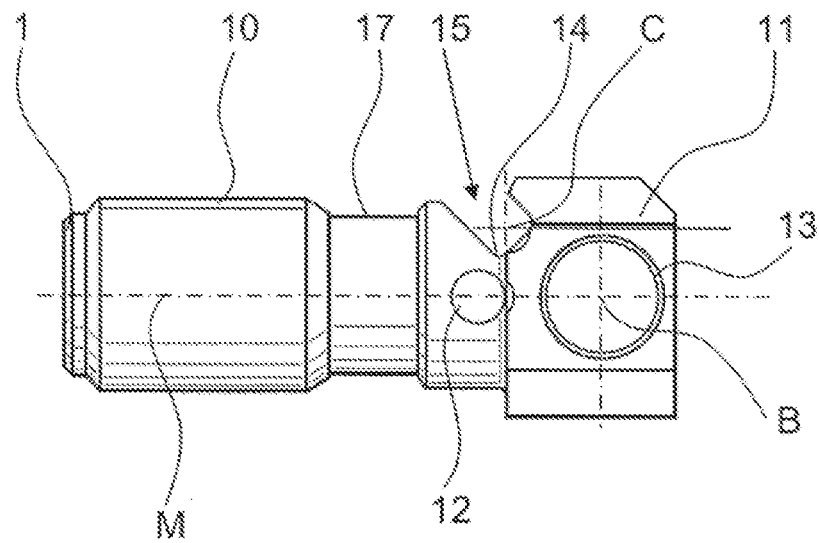
FIG. 3 shows a side view of a bolt to fix a wire to a plate of an external fixator, whereby the bolt is equipped with anti-torque elements.
Figure 4:
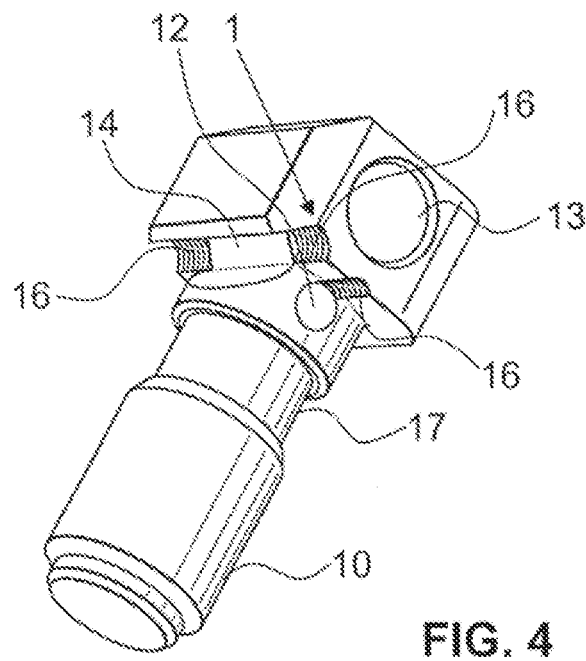
FIG. 4 shows a perspective view of the bolt according to FIG. 3.

FIGS. 2-4 show a system for fixing wire 4 to an external fixator element 3 such as a ring or a plate. The system comprises:

external fixator element 3 having at least one surface 31 and at least one opening 30 extending from surface 31, a wire 4 adapted to extend through bony structure and to be fastened to surface 31, a bolt 1 having a shaft which comprises a threaded section 10, a head section 11 and at least one clamping element 12, 14 wherein bolt 1 is adapted to extend through opening 30 and the at least one clamping element 12, 14 accommodates and clamps a wire to surface 31 with a clamping force, a nut 7 to pull bolt 1 against surface 31 the external fixator element 3 with a clamping force, and a counter torque tool 2 to provide a counter torque while fastening wire 4 with bolt 1 and nut 7 to surface 31 wherein bolt 1 comprises a counter torque opening 13 and counter torque tool 2 comprises a bolt section 20 which is adapted to engage into counter torque opening 13 of the bolt, and wherein bolt section 20 has preferably a cross-section which is complementary to counter torque opening 13.

FIG. 2 shows a perspective view of a possible application of the bolt 1 and the counter-torque tool 2. Several wires 4 extend through bony structure 8. Wires 4 are fixed to the fixation plate 3 by means of a bolt 1 and nut 7. Thereby wire 4 will be clamped by means of the clamping elements 12, 14 against the surface 31 of fixation plate 3 as an axial clamping force is provided upon tightening nut 7.

Figure 5:
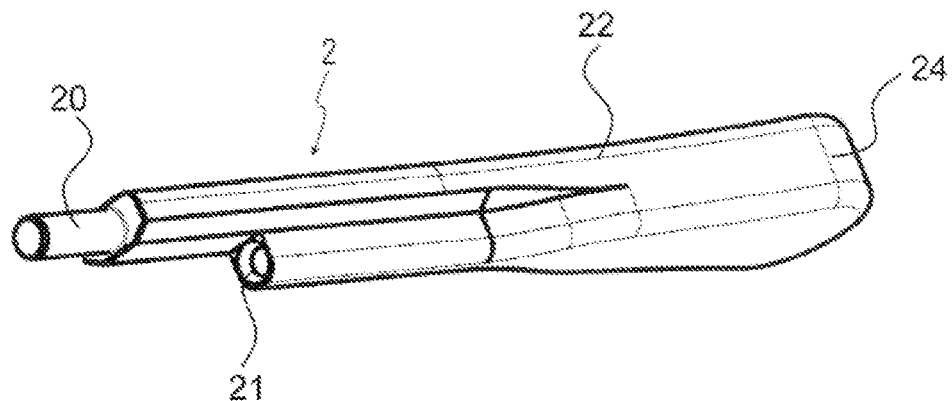
FIG. 5 shows a perspective view of a first embodiment of a counter torque tool to provide a counter torque while fastening a wire with a bolt according FIGS. 3 and 4.
Figure 6:
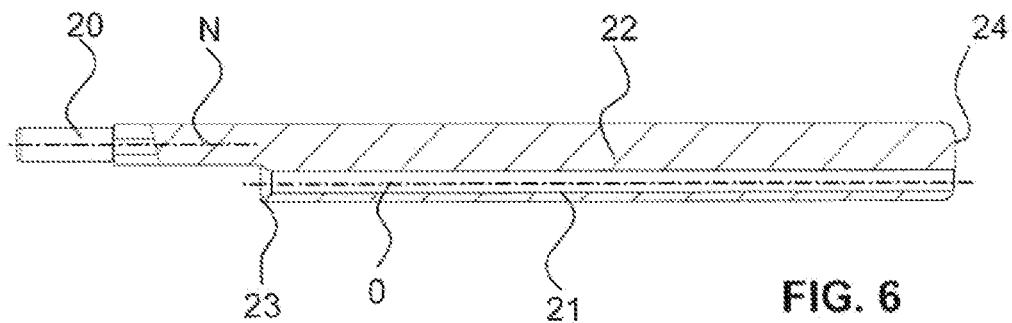
FIG. 6 shows a sectional view of the tool according to FIG. 5.
Figure 7:
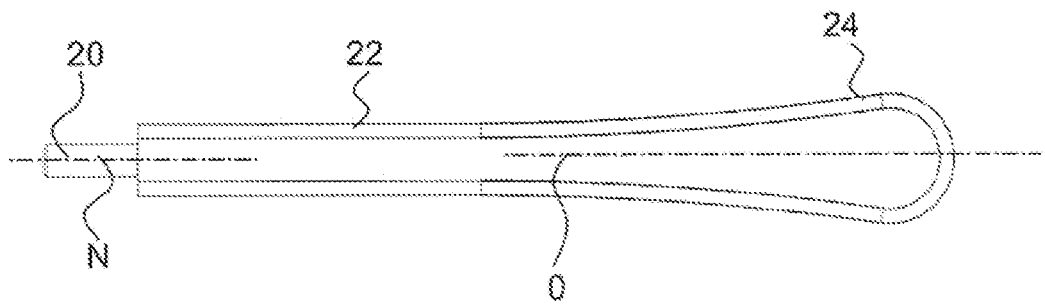
FIG. 7 shows a top-view of the tool according to FIG. 5.

To the left of FIG. 2 bolt 1 is in connection with a counter torque tool 2 having a handle 22 as it shown in FIGS. 5 to 7. Thereby the counter torque tool 2 engages with its bolt section 20 into the counter torque opening 13 of bolt 1.

To the right of FIG. 2 the bolt 1 is in connection with a counter torque tool 2a which is in connection with a wire tensioner 5. Thereby the counter torque tool 2a is arranged in front of the wire tensioner with which the surgeon is able to tension wire 4 and to provide also the counter torque, when the nut 7 is being tightened.

With regard to FIG. 2 it has also been noted the axis A of the counter torque opening 13 can also extend at an angle to the middle axis M of bolt 1. Preferably the axis A of the counter torque opening extends collinear to wire 4.

From the description above it becomes clear that wire 4 is preferably clamped by means of bolt 1 and a respective surface 31 of fixation plate 3. However, it is also possible to arrange a separate element which provides also an opening through which the bolt 1 extends and a respective surface against the wire 4 can be clamped. Such a separate element can be used to arrange the wire with an offset to the plate. This is shown with wire 4' in FIG. 2 which is spaced above surface 31.

FIGS. 3 and 4 show a bolt 1 to connect a wire to a fixation plate of an external fixation system. Such external fixation systems usually comprise at least two plates which are connected by means of length-adjustable rods or struts in order to orient the plates with respect to the each other. The plates are in connection with tensioned wires or with pins which extend trough or in bony structure. The tensioned wires are mounted to the plates by means of the bolt 1. The bolt 1 can also be used to clamp a pin to the plate. The pin or wire is thereby clamped by means of a clamping element 12, 14 in the bolt and the respective surface of the plate on which the wire or pin lies.

The preferred bolt 1 according to FIGS. 3 and 4 comprises a shaft having a threaded section 10, a head section 11 and clamping elements 12, 14 to accommodate and to clamp a tensioned or to be tensioned wire of an external fixator system. The clamping elements 12, 14 can have the shape of a clamping opening 12 and/or a clamping channel 14. The threaded section 10 and the head section 11 extend along a middle axis M. Thereby the threaded section 10 can be followed directly by the head section 11 or an additional section, such as a reduced shaft section 17, can be arranged between the threaded section 10 and the head section 11. The shaft is adapted to extend through an opening 30 of the fixation plate 3. The wire 4 is clamped by means of the clamping element 12, 14 and by means of surface 31 of the fixation plate 3.

A wire or pin extends through or in the clamping elements 12, 14. Thereby it is in contact with the respective surface 31. The bolt 1 itself extends through opening 30 within a fixation plate. Thereby the wire lies on the top side of the fixation plate and is clamped towards the top side. The bolt 1 is secured by a nut which is in contact with the threaded section and the bottom side of the fixation plate. In other words: Upon tightening nut 7, the head 11 of bolt 1 will be moved towards the top side of the fixation plate and the wire will be clamped by top side 31 and the clamping elements 12, 14. However, it is important that the torque that has to be applied onto the nut upon tightening the same will be compensated on the bolt in order to prevent the aligned wire 4 from becoming misaligned. Hence, a rotation of the bolt 1 around its middle axis M has to be prevented. In order to compensate for the torque a respective counter torque has to be applied. The counter torque can be applied by a counter torque tool 2 through counter torque opening 13 of the bolt 1. In other words, bolt 1 comprises a counter torque opening 13 to accommodate a counter torque tool 2.

Preferably the opening 13 is arranged in the head section 11 of the bolt 1. The opening 13 extends along an axis A which is arranged at an angle to the middle axis M. Preferably axis A is perpendicular to middle axis M which means that the opening 13 extends perpendicular to bolt 1. The opening 13 can be provided in several forms, such as a through opening which extends completely through the bolt 1 or a blind opening extending only partly into the head of bolt 1. The opening 13 can also have an open part, so that a slot-like structure results which is accessible from the top of head section 11. With regard to the cross section the opening 13 has a similar cross-section as the respective of the counter torque tool 2 as explained below. Preferably the opening 13 has a circular cross-section which allows flexibility with regard to the orientation of the counter torque tool. Alternatively the opening 13 may also be provided with a square, rectangular, polynomic, elliptical or quadratic cross-section.

The bolt as shown in FIGS. 3 and 4 comprises two clamping elements, namely the clamping opening 12 and the clamping channel 14. However, it is also possible to provide only one of the clamping elements 12, 14. The opening 12 as well as the channel 14 accommodate a respective wire or pin which is clamped between a wall of the opening 12 or channel 14 and a surface of the fixation plate with which the wire is in contact.

The clamping opening 12 extends in the present embodiment along a middle axis B which extends perpendicular and through the middle axis M. Thereby the clamping opening 12 crosses the middle axis M. Alternatively it may also be arranged such that the middle axis B extends offset form middle axis M.

The clamping channel 14 extends along a middle axis C. Preferable middle axis C is offset from the middle axis M, but parallel to middle axis B in case the clamping opening 12 is present. The clamping channel 14 comprises a cut out 15 via which access is provided to the clamping channel 14. This means that the bolt can be imposed over a wire.

Preferably the clamping opening 12 and/or the clamping channel 15 comprise a friction enhancing structure 16. The friction enhancing structure 16 is arranged near and/or within the respective clamping element 12, 15 and serves to enhance friction between the clamping element 12, 15 and the wire. Thereby the tension force of the wire can be increased by constant pretensioning force of the bolt 1 and the respective nut. The friction enhancing structure 16 is preferably provided as a plurality of grooves which are arranged parallel to each other.

The friction enhancing structure 16 which is arranged with regard to the clamping opening 12 is arranged on a surface on the head section 11 which is directed towards the threaded section 10.

Figure 8:
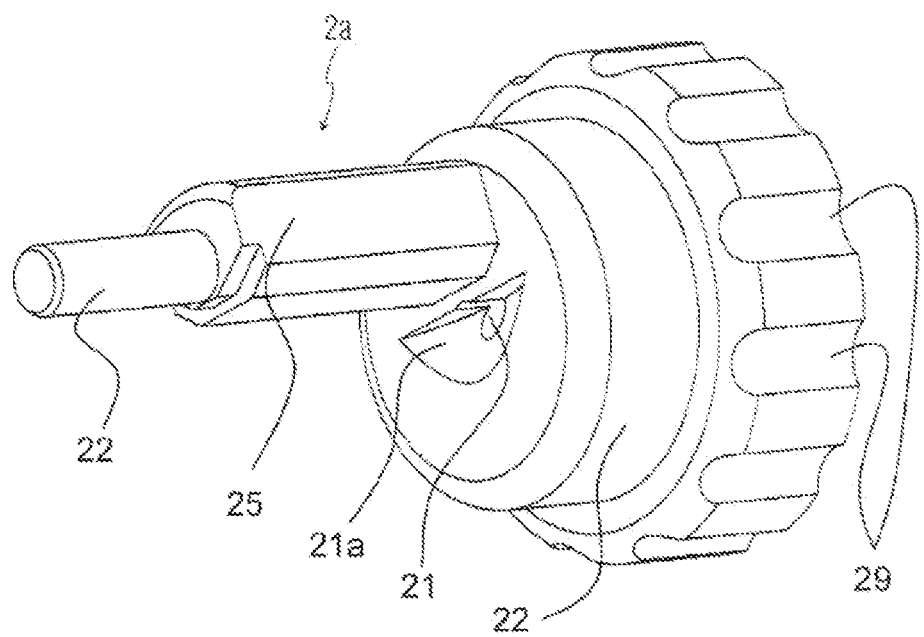
FIG. 8 shows a perspective view of a further embodiment of a counter torque tool to be used with a wire tensioner.
Figure 9:
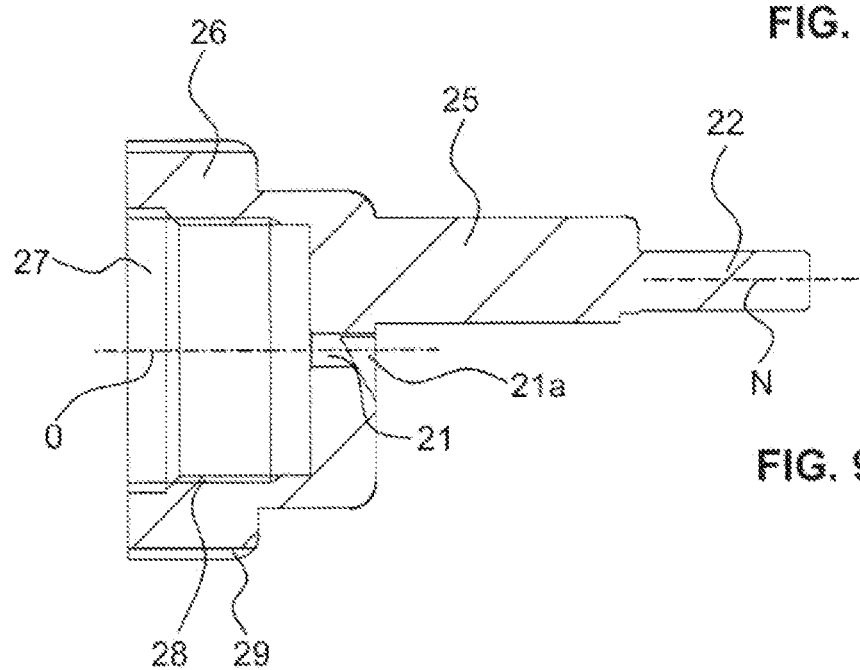
FIG. 9 shows a section view of the counter torque tool according to FIG. 8.

FIGS. 5 to 7 show a first embodiment of a counter torque tool 2 and FIGS. 8 and 9 show a second embodiment. The first embodiment is preferably used to tighten a bolt being in connection with an untensioned wire to the fixation plate. The second embodiment can be used together with a wire tensioner, whereby it is in a fixed connection with the wire tensioner. The latter is particularly advantageous since in the prior art the need of a separate counter torque tool apart from the wire tensioner and the tool to tighten the nut is necessary, which means that the surgeon has to handle three different tools in order to tighten the bolt/nut connection and to tension the wire.

Both of the counter torque tools 2 comprise a bolt section 20 which is adapted to be accommodated by the counter torque opening 13. Via the bolt section 20 the counter torque is applied onto the bolt 1. In the present embodiment the bolt section 20 extends along a middle axis N and has a substantially circular cross-section. The cross-section of the bolt section 20 however, is dependent on the cross-section of the counter torque opening 13. The bolt section 20 may therefore have any other cross-section as mentioned with regard to the counter torque opening 13.

The first embodiment comprises furthermore a handle 22 which extends from the bolt section 20. The handle 22 can be used by the surgeon to apply the counter torque. Within the handle there is optionally arranged wire opening 21. Wire opening 21 extends at least partly through the handle 22 and serves mainly to receive the wire 4, 4' of the external fixator. The remaining part of the wire extending over the fixation plate or fixation ring is preferably fully received by said wire opening 21 which has the advantage that the risk of injuries for the surgeon due to the wire is limited. The wire opening 21 extends along a middle axis O which is parallel to the middle axis N of the bolt section 22. The diameter of the wire opening 21 is preferably larger than the diameter of the wire which allows very easy handling of the device. Furthermore the distance between the axes N and O needs not to be provided in a narrow tolerance field. The wire opening 21 further comprises furthermore a chamfered edge 23 which allows better insertion of the wire into the opening.

The cross section of the handle 22 preferably expands in one plane as seen from the bolt section 20 towards the other end 24 so that it becomes more ergonomic for the surgeon to grasp the handle 22 in a perpendicular plane. Between the bolt section 20 and the other end 24 the cross section preferably remains constant.

The embodiment of FIGS. 8 to 9 the counter torque tool to be connected to a wire tensioner will now be explained. The bolt section 20 is joined by a transition section 25 having a larger diameter than the bolt section. The transition section 25 is then in contact with a connection section 26 by which the counter torque tool is connected to the wire tensioner. The connection section 26 comprises an opening 27 which has a thread 28. On the outer surface the connection section 26 are with several grooves 29 which serves to connect the counter torque tool to a wire tensioner.

Also the second embodiment comprises a wire opening 21 extending along middle axis O which is parallel to middle axis N. Via the wire opening 21 the wire will be engaged into the wire tensioner. Also opening 21 may comprise a chamfered edge similar to 23 as shown in FIG. 6. In FIG. 8, in front of the wire opening 21, an insertion aid 21a is provided in the shape of a conical recess having a diameter that decreases towards the opening 21.

The use of such a counter torque tool 2 with a wire tensioner has the advantage that the surgeon can easily tighten the bolt and with, regard to misalignments, in a secure manner. Thereby the surgeon has to tension the wire with the wire tensioner which is during tensioning, in contact with the bolt 1 via the counter torque section 22. Due to this contact the wire tensioner and the bolt are already aligned with respect to the direction of the wire. Furthermore the wire tensioner is no longer freely moveable which means that the surgeon does not have to carry the whole weight of the wire tensioner. Once the wire is tensioned the bolt has to be secured by a nut. Thereby the nut will be tightened by means of a single wrench or a similar tool and via the wire tensioner the counter torque will be provided.

Preferably the counter torque tool 2 is made of a metallic material, such as stainless steel or titanium. Preferably the bolt 1 is made of a metallic material, such as stainless steel or titanium.

FIGS. 10-14 show a bolt 100 and a washer 200 as provided in a system for fixing a position of a wire with respect to a ring member of an external fixation frame, the ring member having top and bottom surfaces.

Figure 10:
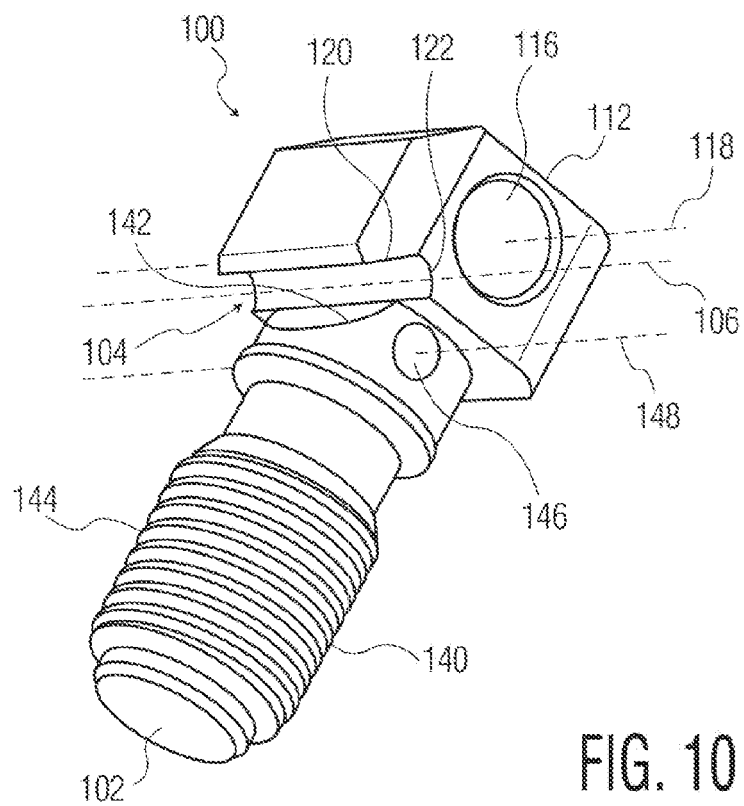
FIG. 10 shows a perspective view of another embodiment of a bolt of the present invention.
Figure 11:
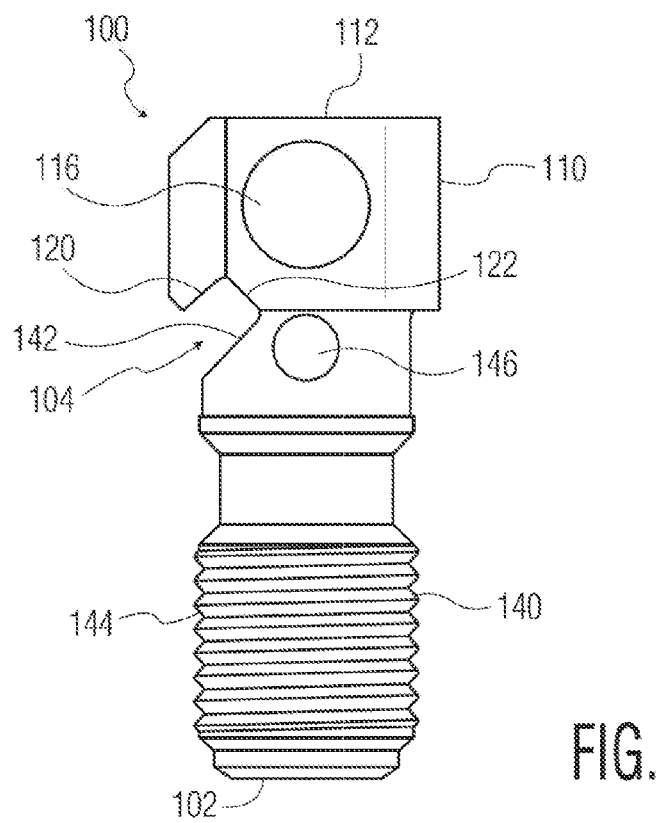
FIG. 11 shows a front view of the bolt shown in FIG. 10.

As shown in FIGS. 10-11, bolt 100 includes a head portion 110 and a shaft portion 140 along a longitudinal axis 102 thereof. Bolt 100 includes a recess 104 therein, the recess having a longitudinal axis 106 transverse and offset to longitudinal axis 102 of bolt 100.

The head portion 110 of bolt 100 includes a top surface 112, a bottom surface 114, and a borehole 116 therethrough, borehole 116 having a longitudinal axis 118 perpendicular to longitudinal axis 102 of bolt 100. Recess 104 runs along an entire length of bottom surface 114 of head portion 110. Recess 114 is at least partially bounded by two flat angled surfaces 120, 122 adjacent bottom surface 114 of head portion 110.

The shaft portion 140 of bolt 100 includes an angled flat surface 142 adjacent the two flat angled surfaces 120, 122 adjacent bottom surface 114 of head portion 110. Shaft portion 140 further includes a threaded section 144 along at least a portion of a length thereof. Shaft portion 140 further includes a borehole 146 therethrough, borehole 146 having a longitudinal axis 148 perpendicular to longitudinal axis 102 of bolt 100. In some embodiments, shaft portion 140 does not include borehole 146.

Figure 12:
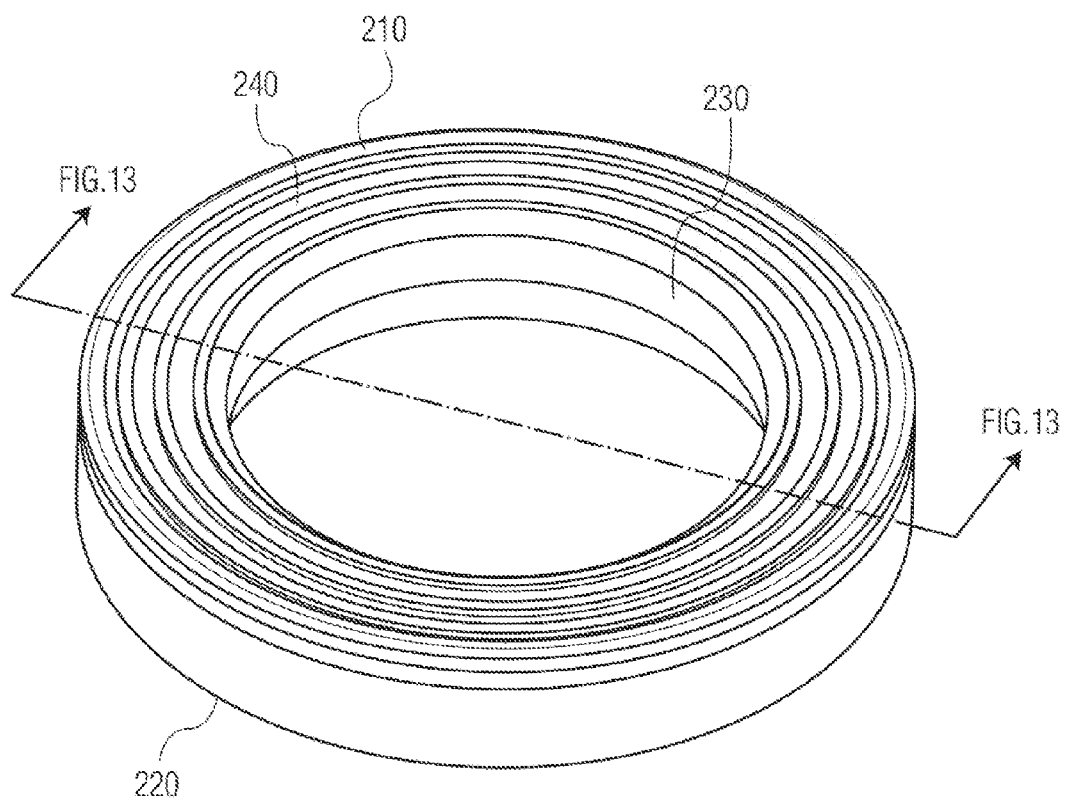
FIG. 12 shows a perspective view of one embodiment of a washer of the present invention used to clamp a fixation wire between a top surface thereof and the bolt shown in FIG. 10.
Figure 13:
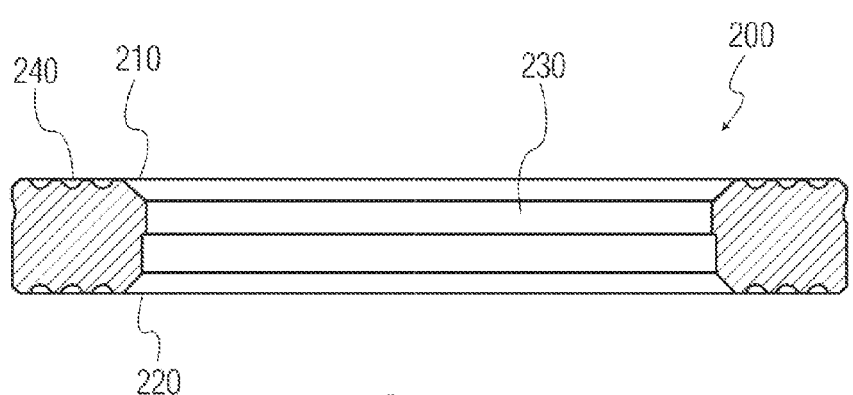
FIG. 13 shows a cross-sectional view along line A-A of the washer shown in FIG. 12.
Figure 14:
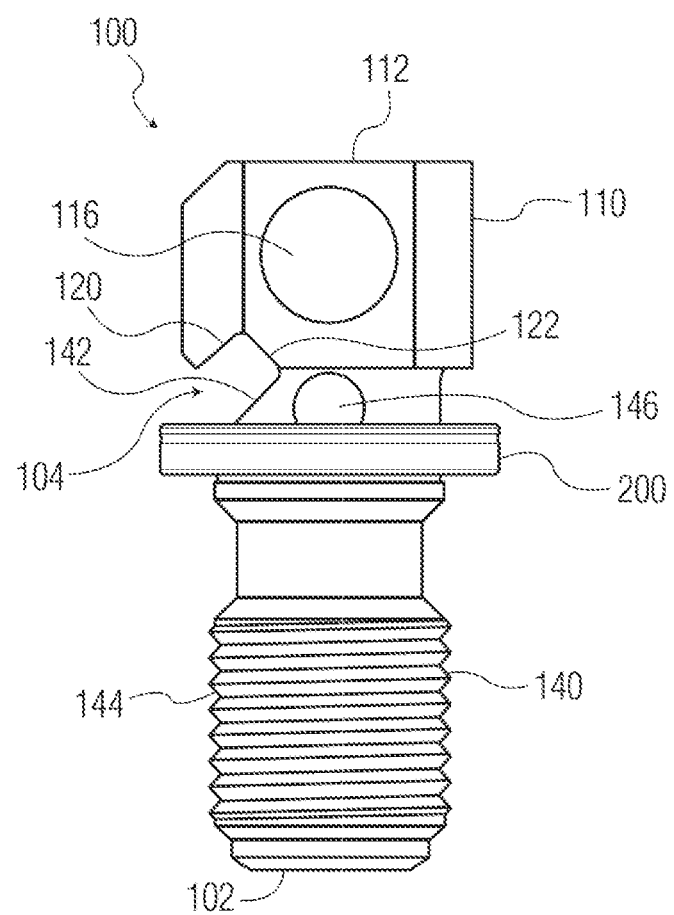
FIG. 14 shows the washer of FIG. 12 in one assembled position to the bolt of FIG. 10.

As shown in FIGS. 12-13, washer 200 includes a top surface 210 and a bottom surface 220. Washer 200 includes a borehole 230 through the top and bottom surfaces 210, 220 thereof. Top surface 210 includes a friction enhancing structure 240 such as grooves that form a roughened surface. These grooves may be located on at least a portion of the top surface 210 of washer 200 but may be located on the entire top surface 210 of washer 200. These grooves may be located on at least a portion of the bottom surface 220 of washer 200 but may be located on the entire bottom surface 220 of washer 200. Preferably, washer 200 includes two grooves on the surface that will be in contact with a wire. Two grooves on this surface generally enhances the fatigue resistance in the wire. In some embodiments, washer 200 may have more or less than two grooves on the friction enhancing structure 240 depending on the wire retaining and fatigue resistance properties desired for a particular surgical need.

In use, shaft portion 140 of bolt 100 is adapted to extend through borehole 230 of washer 200 as shown in FIG. 13 and an opening within a fixation plate or ring member 3 as shown in FIGS. 1-2, for example, of an external fixation frame when the bottom surface 220 of washer 200 lies adjacent to a top surface of the ring member. A portion of a fixation wire, such as wire 4', for example, is at least partially received within recess 114 of head portion 110 of bolt 100 and is clamped between head portion 110 of bolt 100 and top surface 210 of washer 200 as a nut (not shown) is threaded on threaded section 144 of shaft portion 140 of bolt 100 and a top surface of the nut becomes engaged to the bottom surface of the ring member.

When the wire is at least partially received within the recess 114 of bolt 110, the wire is at least partially surrounded by the two flat angled surfaces 120, 122 adjacent the bottom surface 114 of head portion 110 of bolt 100 and the angled flat surface 142 of shaft portion 140 of bolt 100. When the wire is clamped between head portion 110 of bolt 100 and top surface 210 of washer 200, an outer surface of the wire is contacted on at least three locations around the perimeter thereof, the three locations being the two angled surfaces 120, 122 adjacent the bottom surface of the head portion 110 of bolt 100 and the roughened surface 240 on at least a portion of the top surface 210 of washer 200. Because recess 104 of bolt 100 is offset from a longitudinal axis 102 thereof, when the wire is at least partially housed within recess 104 the outer surface of the wire does not span borehole 230 of washer 200. Rather, the outer surface of the wire contacts roughened surface 240 approximately 60° around the perimeter of the washer.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for fixing a position of a wire with respect to a ring member of an external fixation frame, the ring member having top and bottom surfaces, the system comprising:
    a bolt having a head portion and a shaft portion along a longitudinal axis thereof, the bolt having a recess at least partially bounded by two angled surfaces adjacent a bottom surface of the head portion, the recess having a longitudinal axis transverse and offset to the longitudinal axis of the bolt, the shaft portion of the bolt including a threaded section; and
    a washer having a top surface and a bottom surface and a borehole through the top and bottom surfaces, the top surface of the washer including a roughened surface on at least a portion thereof,
    wherein the shaft portion of the bolt is adapted to extend through an opening within the ring member of the external fixation frame, and
    wherein a portion of the wire is at least partially received within the recess of the bolt and is clamped between the head portion of the bolt and the top surface of the washer such that an outer surface of the wire is contacted on at least three locations thereof, the three locations being the two angled surfaces adjacent the bottom surface of the head portion and the roughened surface on at least a portion of the top surface of the washer as a nut is threaded on the threaded section of the shaft portion and a top surface of the nut becomes engaged to the bottom surface of the ring member.

2. The system of claim 1, wherein the shaft portion of the bolt includes an angled flat surface adjacent the two flat angled surfaces adjacent the bottom surface of the bolt such that when a portion of the wire is at least partially received within the recess of the bolt, the wire is at least partially surrounded by the two flat surface adjacent the bottom surface of the head portion of the bolt and the angled flat surface of the shaft portion of the bolt.

3. The system of claim 1, wherein the recess of the bolt runs along an entire length of the bottom surface of the head portion.

4. The system of claim 1, wherein the longitudinal axis of the recess of the bolt is perpendicular to the longitudinal axis of the bolt.

5. The system of claim 1, wherein the shaft portion of the bolt includes a first borehole therethrough, the first borehole having a longitudinal axis perpendicular to the longitudinal axis of the bolt.

6. The system of claim 5, wherein the head portion of the bolt includes a second borehole therethrough, the second borehole having a longitudinal axis perpendicular to the longitudinal axis of the bolt.

7. The system of claim 6, wherein a diameter of the second borehole of the head portion of the bolt is larger than a diameter of the first borehole of the shaft portion of the bolt.

8. A system for fixing a position of a wire with respect to a ring member of an external fixation frame, the ring member having top and bottom surfaces, the system comprising:
  a bolt having a head portion and a shaft portion along a longitudinal axis thereof, the head portion of the bolt including top and bottom surfaces, the bottom surface of the head portion of the bolt having a recess therein along an entire length thereof, the recess at least partially bounded by two angled surfaces adjacent a bottom surface of the head portion and having a longitudinal axis transverse and offset to the longitudinal axis of the bolt, the shaft portion of the bolt including a threaded section; and
  a washer having a top surface and a bottom surface and a borehole through the top and bottom surfaces, the top surface of the washer including a roughened surface on at least a portion thereof,
  wherein the shaft portion of the bolt is adapted to extend through the borehole of the washer and an opening within the ring member of the external fixation frame when the bottom surface of the washer lies adjacent to the top surface of the ring member, and
  wherein a portion of the wire is at least partially received within the recess of the head portion of the bolt and is clamped between the head portion of the bolt and the top surface of the washer such that an outer surface of the wire is contacted on at least three locations thereof, the three locations being the two angled surfaces adjacent the bottom surface of the head portion and the roughened surface on at least a portion of the top surface of the washer as a nut is threaded on the threaded section of the shaft portion and a top surface of the nut becomes engaged to the bottom surface of the ring member.

9. The system of claim 8, wherein the shaft portion of the bolt includes an angled flat surface adjacent the two flat surfaces adjacent the bottom surface of the bolt such that when a portion of the wire is at least partially received within the recess of the head portion of the bolt, the wire is at least partially surrounded by the two flat surface adjacent the bottom surface of the head portion of the bolt and the angled flat surface of the shaft portion of the bolt.

10. The system of claim 8, wherein the longitudinal axis of the recess of the bolt is perpendicular to the longitudinal axis of the bolt.

11. The system of claim 8, wherein the shaft portion of the bolt includes a first borehole therethrough, the first borehole having a longitudinal axis perpendicular to the longitudinal axis of the bolt.

12. The system of claim 11, wherein the head portion of the bolt includes a second borehole therethrough, the second borehole having a longitudinal axis perpendicular to the longitudinal axis of the bolt.

13. The system of claim 12, wherein a diameter of the second borehole of the head portion of the bolt is larger than a diameter of the first borehole of the shaft portion of the bolt.

14. A system for fixing a position of a wire with respect to a ring member of an external fixation frame, the ring member having top and bottom surfaces, the system comprising:
  a bolt having a head portion and a shaft portion along a longitudinal axis thereof, the head portion of the bolt including top and bottom surfaces, the bottom surface of the head portion of the bolt having a recess therein, the recess being at least partially bounded by two flat angled surfaces adjacent the bottom surface of the head portion, the recess having a longitudinal axis transverse and offset to the longitudinal axis of the bolt, the shaft portion of the bolt including a threaded section;
  a washer having a top surface and a bottom surface and a borehole through the top and bottom surfaces, the top surface of the washer including a roughened surface on at least a portion thereof; and
  a nut having top and bottom surfaces,
  wherein the shaft portion of the bolt is adapted to extend through the borehole of the washer and an opening within the ring member of the external fixation frame when the bottom surface of the washer lies adjacent to the top surface of the ring member, and
  wherein a portion of the wire is at least partially received within the recess of the bolt and is clamped between the head portion of the bolt and the top surface of the washer such that an outer surface of the wire is contacted on at least three locations thereof, the three locations being the two angled surfaces adjacent the bottom surface of the head portion and the roughened surface on at least a portion of the top surface of the washer as the nut is threaded on the threaded section of the shaft portion and the top surface of the nut becomes engaged to the bottom surface of the ring member.

15. The system of claim 14, wherein the shaft portion of the bolt includes an angled flat surface adjacent the two flat surfaces adjacent the bottom surface of the bolt such that when a portion of the wire is at least partially received within the recess of the head portion of the bolt, the wire is at least partially surrounded by the two flat surface adjacent the bottom surface of the head portion of the bolt and the angled flat surface of the shaft portion of the bolt.

* * * * *